(12) United States Patent
Milverton

(10) Patent No.: US 12,090,045 B2
(45) Date of Patent: Sep. 17, 2024

(54) INTRAOCULAR LENS

(71) Applicant: StabiLens Pty Ltd, Buradoo (AU)

(72) Inventor: Edward John Milverton, Buradoo (AU)

(73) Assignee: StabiLens Pty Ltd, Buradoo (AU)

( * ) Notice: Subject to any disclaimer, the term of this patent is extended or adjusted under 35 U.S.C. 154(b) by 0 days.

(21) Appl. No.: 17/553,157

(22) Filed: Dec. 16, 2021

(65) Prior Publication Data
US 2022/0104938 A1    Apr. 7, 2022

Related U.S. Application Data

(63) Continuation of application No. 16/759,259, filed as application No. PCT/AU2018/051118 on Oct. 15, 2018, now Pat. No. 11,246,702.

(30) Foreign Application Priority Data

Oct. 25, 2017  (AU) ................................ 2017904314
Jan. 11, 2018  (AU) ................................ 2018900082

(51) Int. Cl.
*A61F 2/16*    (2006.01)

(52) U.S. Cl.
CPC .......... *A61F 2/1645* (2015.04); *A61F 2/1618* (2013.01); *A61F 2002/16901* (2015.04)

(58) Field of Classification Search
CPC .................. A61F 2/1645; A61F 2/1618; A61F 2002/16901
See application file for complete search history.

(56) References Cited

U.S. PATENT DOCUMENTS

| | | | |
|---|---|---|---|
| 4,437,194 | A | 3/1984 | Hahs |
| 4,706,666 | A | 11/1987 | Sheets |
| 6,228,115 | B1 | 5/2001 | Hoffmann et al. |
| 6,261,321 | B1 | 7/2001 | Kellan |
| 7,435,259 | B2 | 10/2008 | Cumming |

(Continued)

FOREIGN PATENT DOCUMENTS

| | | |
|---|---|---|
| WO | 99/62434 A1 | 12/1999 |
| WO | 2015047227 A1 | 4/2015 |

OTHER PUBLICATIONS

Office Action for Japanese Application No. 2020-543655, mailed Oct. 25, 2022, 11 pages.

(Continued)

*Primary Examiner* — Jerrah Edwards
*Assistant Examiner* — Aren Patel
(74) *Attorney, Agent, or Firm* — Sterne, Kessler, Goldstein & Fox P.L.L.C.

(57) ABSTRACT

An intraocular lens comprising an optic and four haptics extending from the optic, each haptic having a proximal end meeting with the optic at differing points about a periphery of the optic. The four haptics are arranged into a first pair comprising two arcuate haptics with curvature orientated toward each other such that a distal end of each of the two haptics of the first pair are in nearer relation than their proximal ends; and, a second pair comprising two arcuate haptics with curvature orientated toward each other such that a distal end of each of the two haptics of the second pair are in nearer relation than their proximal end.

13 Claims, 4 Drawing Sheets

(56) References Cited

U.S. PATENT DOCUMENTS

| | | | |
|---|---|---|---|
| 2003/0018386 A1* | 1/2003 | Laguette | A61F 2/16 623/6.49 |
| 2006/0142855 A1 | 6/2006 | Vaudant et al. | |
| 2007/0005136 A1 | 1/2007 | Richardson | |
| 2007/0027539 A1* | 2/2007 | Pynson | A61F 2/1613 623/6.46 |
| 2008/0183289 A1 | 7/2008 | Werblin | |
| 2009/0264998 A1* | 10/2009 | Mentak | A61F 2/1627 623/6.37 |
| 2011/0238174 A1 | 9/2011 | Hong et al. | |
| 2014/0094909 A1 | 4/2014 | Cumming | |
| 2014/0172094 A1 | 6/2014 | Kahook et al. | |
| 2014/0336757 A1* | 11/2014 | Simonov | A61F 2/1651 623/6.34 |
| 2015/0272725 A1* | 10/2015 | Camargos | A61F 2/16 623/6.49 |
| 2017/0071728 A1 | 3/2017 | Shahinpoor et al. | |
| 2018/0055626 A1* | 3/2018 | Beer | A61F 2/1629 |

OTHER PUBLICATIONS

International Search Report issued in corresponding International Application No. PCT/AU2018/051118, mailed Nov. 21, 2018.
Extended European Search Report issued in European Application No. 18871604.7, mailed Jul. 8, 2021, 7 pages.

\* cited by examiner

INTRAOCULAR LENS

TECHNICAL FIELD

The present invention generally relates to an intraocular lens having haptics.

BACKGROUND

Intraocular lenses are artificial lenses that may be implanted in the eye in a surgical procedure to replace the natural lens of the eye. A typical intraocular lens may feature an artificial lens termed an optic, as well as one or more support members termed haptics to position the intraocular lens within the capsular bag of the eye.

Certain optics may require a greater degree of centration and stability within the eye, for example toric lenses which have different powers in different meridians of the lens. The rotational stability of toric lenses may be particularly important, with each degree of rotation of a toric lens reducing refractive performance by approximately 3%. Other optics which may require a high degree of centration and stability within the eye may include bi-focal and multi-focal lenses.

There is a need for intraocular lenses with haptics that improve the stability of the optic within the capsular bag of the eye. For example, there is a need for a toric intraocular lens with improved rotational stability within the capsular bag of a patient after implantation.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

BRIEF SUMMARY

The present invention seeks to provide an invention with improved features and properties.

In an aspect the present invention provides an intraocular lens comprising an optic and four haptics extending from the optic, each haptic having a proximal end meeting with the optic at differing points about a periphery of the optic.

Preferably the four haptics are arranged into: a first pair comprising two arcuate haptics with curvature orientated toward each other such that a distal end of each of the two haptics of the first pair are in nearer relation than their proximal ends; and, a second pair comprising two arcuate haptics with curvature orientated toward each other such that a distal end of each of the two haptics of the second pair are in nearer relation than their proximal end.

Preferably the optic periphery is circular.

Preferably both haptics of the first pair meet with the optic perimeter at a first semicircular region of the optic and both haptics of the second pair meet with the optic perimeter at a second semicircular region of the optic, wherein the first and second semicircular regions do not overlap.

Preferably each haptic meets with the optic periphery at a separate quadrant of the optic.

Preferably the first pair of optics meet at adjacent quadrants and the second pair of haptics meet at adjacent quadrants.

Preferably the haptics of the first pair have generally opposing concavities and the haptics of the second pair have generally opposing concavities.

Preferably the haptics have a thin, elongate form.

Preferably the haptics have a solid cross section across the entire span of the haptics.

Preferably the intraocular lens is of one-piece construction.

Preferably an outer edge of at least one of the haptics has a rounded bulge.

Preferably the rounded bulge is configured to engagingly fit into a lacuna of a capsular bag of a patient when in use.

Preferably the rounded bulge is at the distal end of the haptic.

Preferably the intraocular lens is formed of a foldable material.

Preferably the foldable material has memory.

Preferably the intraocular lens formed of a foldable material is suitable for use with a preloaded injection system.

In an aspect the present invention provides an intraocular lens comprising an optic with a circular perimeter with a first semicircular region and a second semicircular region defined by line X-X, and four arcuate haptics extending from the optic and grouped into a first pair, each haptic of the first pair having a proximal end meeting with the optic perimeter at the first semicircular region and a second pair, each haptic of the second pair having a proximal end meeting with the optic at the second semicircular region.

Preferably the optic has four quadrants defined by line X-X and a line Y-Y intersecting with line X-X at the centre C of the optic, wherein each haptic meets with the optic perimeter at a separate quadrant.

Preferably each of the haptics curve toward line Y-Y such that a distal end of each haptic is nearer to Y-Y than the proximal end Preferably the intraocular lens displays an axis of symmetry about X-X.

Preferably the intraocular lens displays an axis of symmetry about Y-Y.

Preferably an included angle between line A passing through C and a centrepoint of a junction between a haptic and the optic perimeter; and line B passing through C and touching with an extreme of the distal end is between about 30° to about 50°.

Preferably an included angle between line A passing through C and a centrepoint of a junction between a haptic and the optic perimeter; and line B passing through C and touching with an extreme of the distal end is between about 35° to about 45°.

Preferably an included angle between line A passing through C and a centrepoint of a junction between a haptic and the optic perimeter; and line B passing through C and touching with an extreme of the distal end is about 40°.

Preferably the inner edge of the distal end of the haptics are offset from the optic along line B by between about 2 mm to about 3 mm.

Preferably a circle draw through the outer edges of the distal ends of each of the haptics has a diameter of between about 11 mm to about 15 mm.

Preferably the optic has a diameter of between about 5.5 mm to about 6 mm.

Preferably each haptic has a radius of curvature of about 4 mm to about 6 mm.

Preferably the offset between the distal ends of the first pair is between about 2 mm to about 3 mm, and the offset between the distal ends of the second pair is between about 2 mm to about 3 mm.

Preferably the haptics have a span of about 3 mm to about 6 mm.

BRIEF DESCRIPTION OF FIGURES

Example embodiments should become apparent from the following description, which is given by way of example

Figure 1:
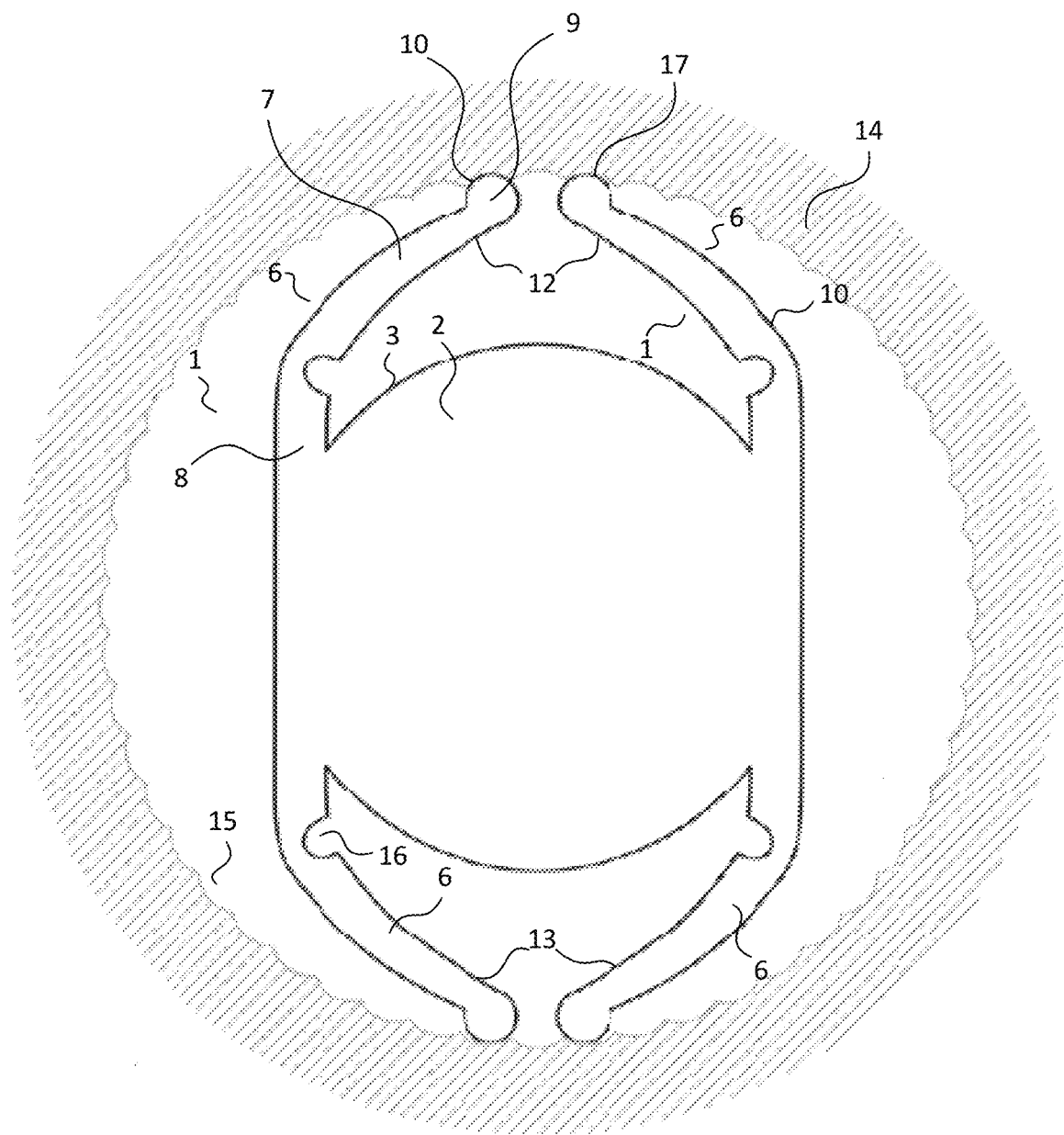
FIG. 1 illustrates an embodiment of an intraocular lens according to the present invention in use within the confines of a capsular bag of a patient.

PARTS LIST 1 intraocular lens
2 optic
3 optic periphery
4 first semicircular region
5 second semicircular region
6 haptic
7 main body portion of haptic
8 proximal end of haptic
9 distal end of haptic
10 outer edge of haptic
11 inner edge of haptic
12 first pair of haptics
13 second pair of haptics
14 capsular bag
15 lacunae
16 recess
17 bulge

PREFERRED EMBODIMENTS

The following modes, given by way of example only, are described in order to provide a more precise understanding of the subject matter of a preferred embodiment or embodiments.

In the Figures, incorporated to illustrate features of an example embodiment, like reference numerals are used to identify like parts throughout the Figures.

Referring to FIG. 1 shown is an intraocular lens 1 configured for placement within the capsular bag 14 of a patient's eye. The intraocular lens 1 may comprise an optic 2 with four haptics 6 extending from the optic periphery 3. The optic periphery 3 may be circular or near circular, for example oval-shaped. In the depicted embodiment, the optic periphery 3 is in the form of a circular perimeter such that the optic 2 has a circumference. The haptics 6 may be configured to engage with the capsular bag 14 thereby stabilizing the position of the optic 2 within the capsular bag 14.

Each haptic 6 may have a distal end 9 and a proximal end 8, with the portion of the haptic 6 extending therebetween termed the main body portion 7 of the haptic. The proximal end 8 may meet with the optic periphery 3, and the distal end 9 may engage with the capsular bag 14 when the intraocular lens 1 is in use. In an embodiment, the haptics 6 may be in the form of a long, thin member, having an arcuate character. The arcuate shape of the haptics 6 may alternatively be described as circinate or curve-form. The long, thin nature of the haptics 6 may alternatively be described as filamentary, thread-like, stand-like, fibre-like, slender or elongate, for example. Each of the four haptics 6 may have a proximal end 8 that meets with a different portion of the optic periphery 3. Otherwise stated, each of the haptics 6 may extend from the optic 2 at a different region of the perimeter of the optic 2. The optic periphery 3 may be divided into four equal regions, with each of these equal regions joining with one of the haptics 6.

The four haptics 6 may be characterized into a first pair 12 and a second pair 13. In an embodiment, the two haptics 6 of the first pair 12 may extend from the optic 2 toward a first direction. Similarly, the two haptics 6 of the second pair 13 may extend from the optic 2 toward a second direction. In an embodiment, these first and second directions may be diametrically opposed, or near diametrically opposed, such that the haptics 6 of the first pair 12 extend from the optic 2 toward an opposite, generally opposite or near opposite direction to the direction of extension of the second pair 13.

Each haptic 6 of the first pair 12 may meet the optic periphery 3 at generally opposing portions of the optic periphery 3. For example, in an exemplary embodiment wherein the optic periphery 3 is circular, each haptic 6 of the first pair 12 may meet with the optic periphery 3 toward opposing ends of a first semicircular region 4. In an embodiment, each haptic 6 of the first pair 12 may meet with the optic periphery 3 at different but adjacent quadrants of the optic 2 having a circular periphery/perimeter.

Similarly, each haptic 6 of the second pair 13 may meet the optic periphery 3 at generally opposing portions of the optic periphery 3. For example, in an exemplary embodiment wherein the optic periphery 3 is circular, each haptic 6 of the second pair 13 may meet with the optic periphery 3 toward opposing ends of a second semicircular region 5. In an embodiment, each haptic 6 of the second pair 13 may meet with the optic periphery 3 at different but adjacent quadrants of the optic 2, wherein the quadrants whereby the second pair 13 meet are different to the quadrants whereby the first pair 12 meet.

The two arcuate, curve-form haptics 6 of the first pair 12 may extend from the optic 2 with their curvature orientated toward each other. By this arrangement, the concavities of the two arcuate haptics 6 of the first pair 12 may be orientated toward each other so as to be generally opposing. Also by this arrangement, and further due to the relatively long character of the haptics 6, the distal ends 9 of the two haptics 6 of the first pair 12 may be in nearer relation than their proximal ends 8.

Similarly the two arcuate, curve-form haptics 6 of the second pair 13 may extend from the optic 2 with their curvature orientated toward each other. By this arrangement, the concavities of the two arcuate haptics 6 of the second pair 13 may be orientated toward each other so as to be generally opposing. Also by this arrangement, and further due to the relatively long character of the haptics 6, the distal ends 9 of the two haptics 6 of the second pair 13 may be in nearer relation than their proximal ends 8.

Having a first pair 12 and second pair 13, each of which comprising haptics 6 that curve toward each other with distal ends 9 configured to locate in the lacuna 15 when compressed within the capsular bag 14 may increase the rotational stability of the optic 2. Stability in other degrees of freedom may also result.

Each of the four haptics 6 may have an inner edge 11 and an outer edge 10, where the inner edge 11 is orientated nearer to the optic 2 and the outer edge 10 is orientated nearer to the capsular bag 14 when the intraocular lens 1 is in use. The outer edge 10 of the distal ends 9 may exhibit a bulge compared to the adjoining outer edge 10 of the main body portion 7 of the haptics 6. This bulge may have a rounded character. The dimension of the rounded bulge of the outer edge 10 of the distal ends 9 of the haptics 6 may be configured to engage with a scalloped feature of the periphery of the capsular bag termed the lacunae 15 of the capsular bag 14. In an embodiment, the rounded bulge 17 may be configured with a curved perimeter with a radius of curvature (arc) of about 0.1 mm to about 0.3 mm, or about 0.2 mm, such that the bulge 17 may fit at least partially within a lacuna 15 which may have a scalloped feature with a radius of curvature (arc) of about 0.2 mm. By this arrangement, the bulge of the outer edge 10 of the distal end 9 of the each haptic 6 may at least partially fit within a lacuna 15 of the capsular bag 14, thus aiding to anchor the haptics 6 against the capsular bag 14 to promote stability of the intraocular lens 1.

The intraocular lens 1 including the optic 2 and the haptics 6 may be formed of a resilient foldable material with memory suitable for use with a preloaded injection system. By this arrangement, the intraocular lens 1 may be deformed to reduce in size and/or to alter in shape under an external force, and may subsequently return to an original, un-deformed shape, such as for example the embodiment of FIG. 2, upon withdrawal of the external force. Such a memory material may confer a flexible, spring-like quality to the haptics 6 which may aid in keeping the optic 2 in a central position within the capsular bag 14 of the eye, and may also minimize force applied to the capsular bag 14. Further, the intraocular lens 1 may be of a one-piece design, which may alternatively be termed a unitary design, whereby the optic 2 and each of the haptics 6 are formed from a single continuous material. Further, the each of the four haptics 6 may be of solid construction, whereby any cross section across the entire span of the haptic 6 from the proximal end 8 to the distal end 9 exhibits a solid character without any hollows.

As each flexible, arcuate haptic 6 of both the first and second pair 13 have a curvature spanning from their distal toward each other with their distal ends 9 facing in relatively close relation, compressive forces provided by the capsular bag 14 to the haptics 6 engaged therewith may bring the distal ends 9 of the flexible haptics 6 into nearer relation than may otherwise be the case for the intraocular lens 1 outside of the capsular bag 14 without any external forces applied. The intraocular lens 1 may be configured so that the distal ends 9 of the haptics 6 of each of the first and second pair 13 do not touch when the intraocular lens 1 is confined within the capsular bag 14. In an embodiment, the distal ends 9 of each haptic 6 in both the first and second pair 13 may be configured to be offset by a distance of about 1 mm to about 3 mm when the intraocular lens 1 is in use within the capsular bag 14. Configuring the intraocular lens 1 with an offset between the distal ends 9 of the haptics 6 when confined within the capsular bag 14 may facilitate each distal end 9 engaging with separate lacunae 15, which may aid in stabilizing the position of the intraocular lens 1 within the capsular bag 14. In an embodiment, the intraocular lens 1 may be sized so that a circle drawn around the outer edge 10 of the distal ends 9 of each haptic 6 has a diameter of between about 11 mm to about 15 mm. In an embodiment, the optic 2 diameter may be between about 5.5 mm to about 6 mm. Such arrangements may be suitable for a range of capsular bag 14 diameters between about 9 mm to about 13 mm.

Figure 2:
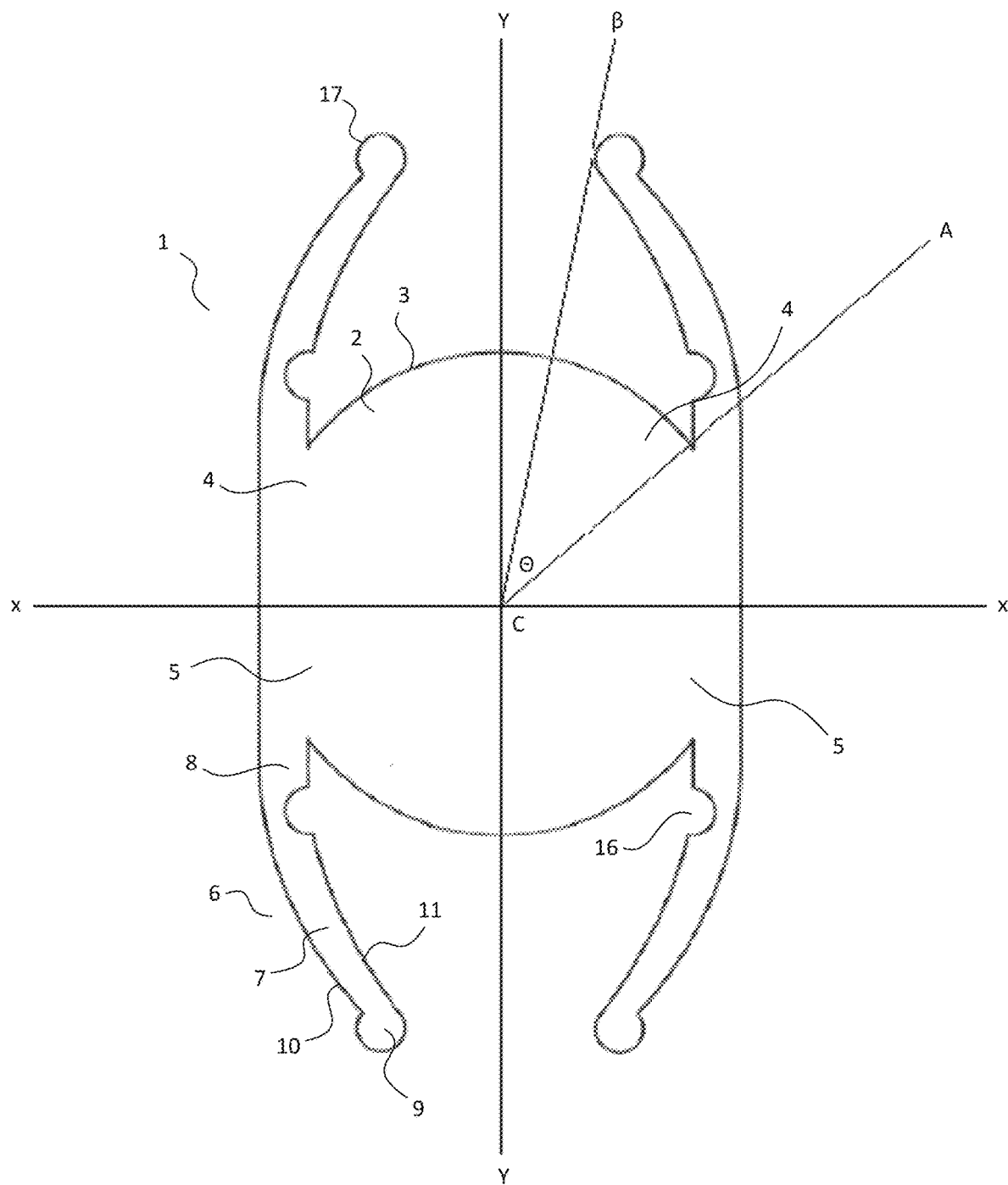
FIG. 2 illustrates an embodiment of an intraocular lens unencumbered by the confines of a capsular bag and free from external forces.
Figure 3:
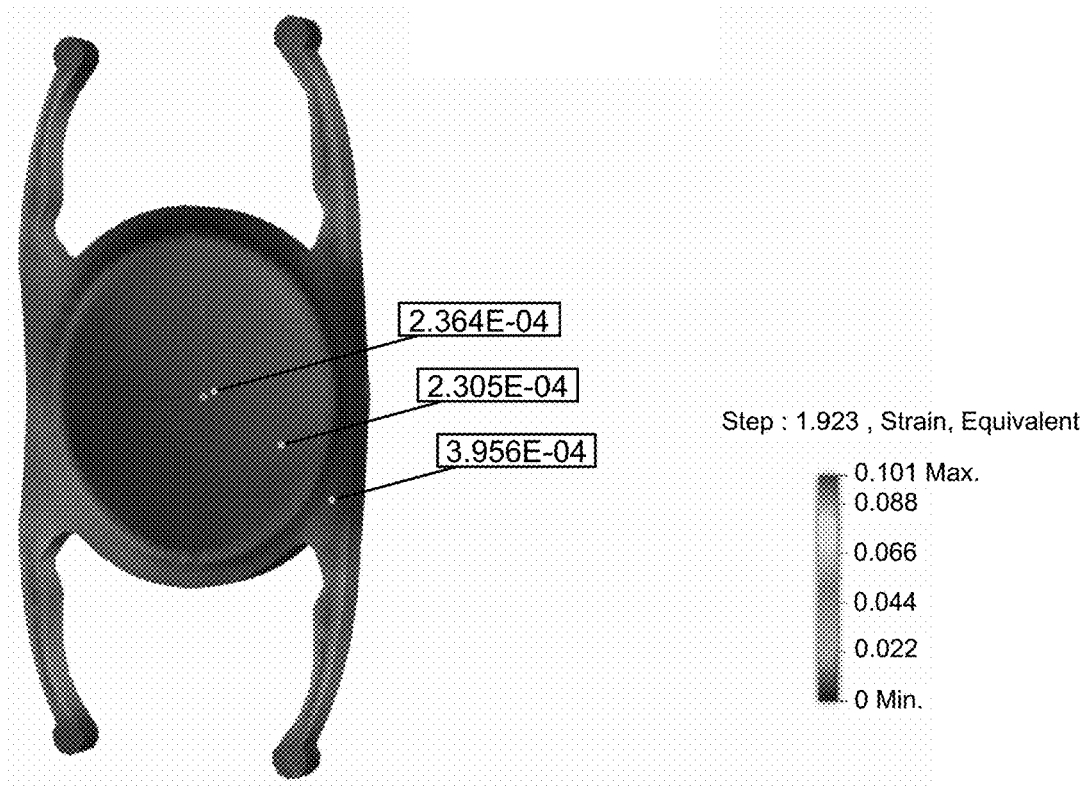
FIG. 3 illustrates an image from an FEM conducted on an intraocular lens according to the present invention.
Figure 4:
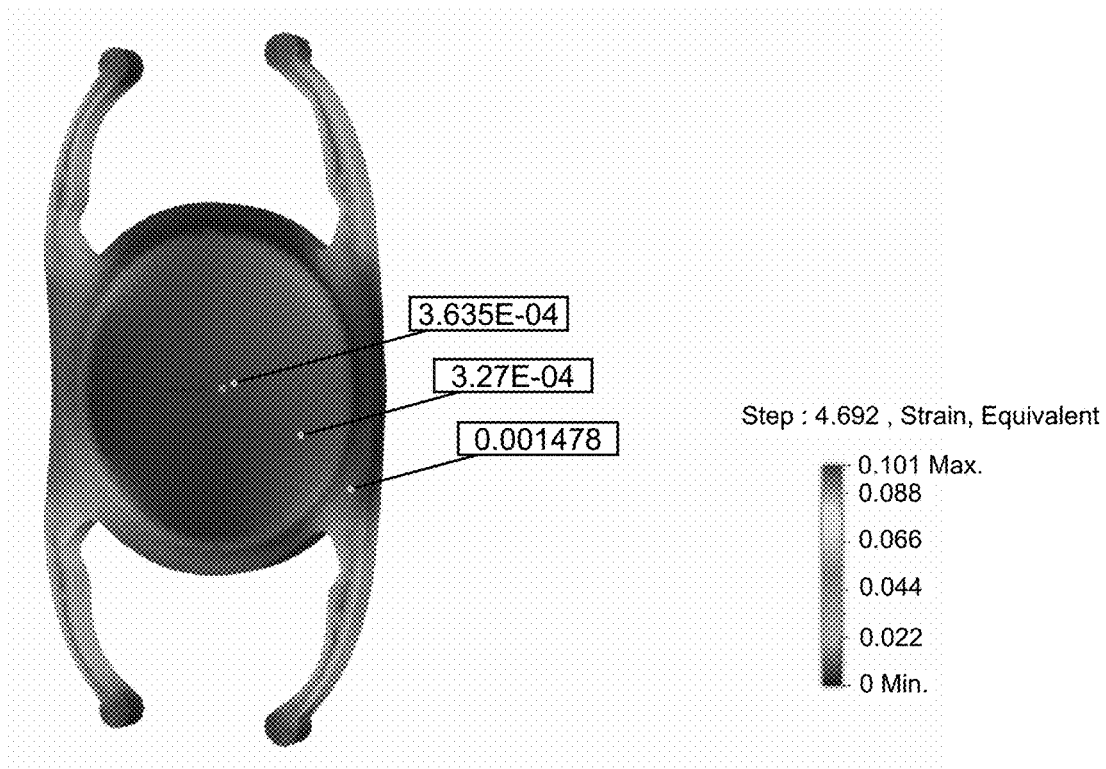
FIG. 4 illustrates a further image from an FEM conducted on an intraocular lens according to the present invention.
Figure 5:
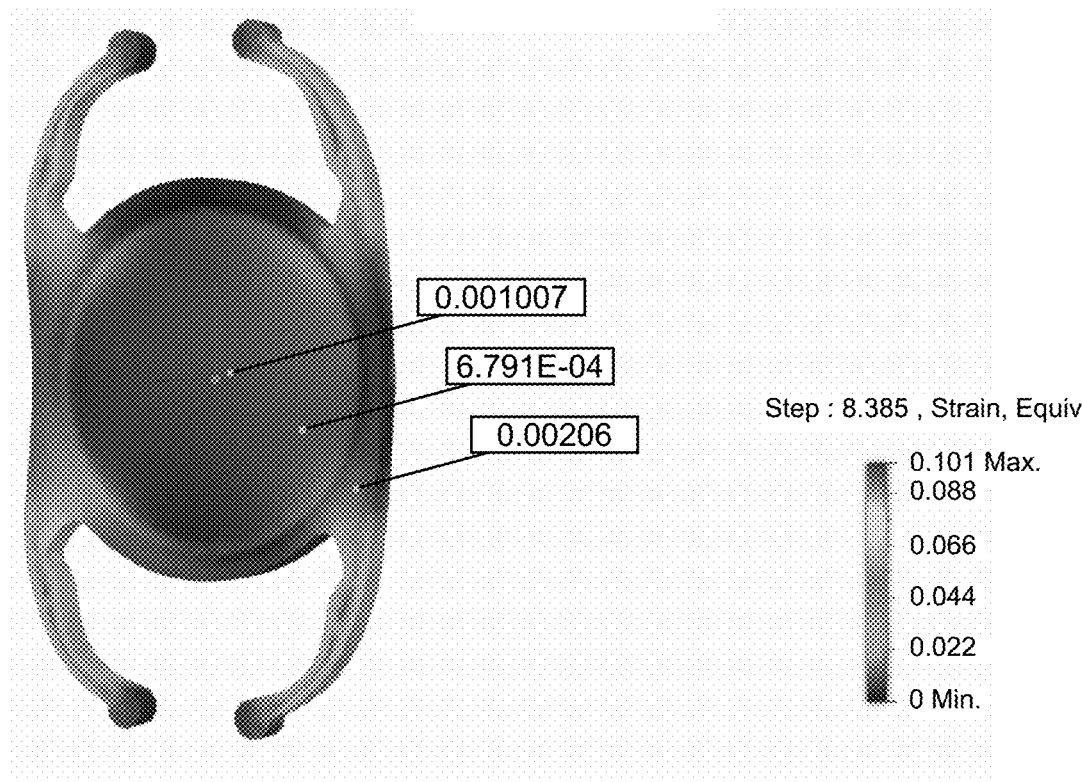
FIG. 5 illustrates a further image from an FEM conducted on an intraocular lens according to the present invention; and, FIG. 6 illustrates a further image from an FEM conducted on an intraocular lens according to the present invention.
Figure 6:
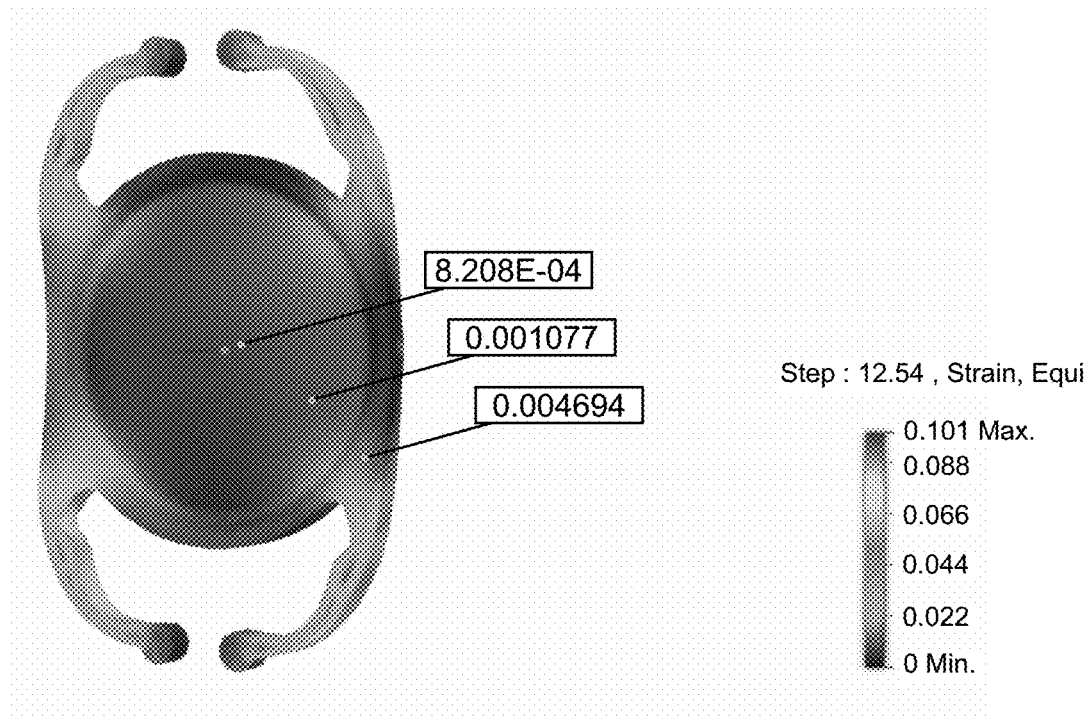

Referring now to FIG. 2, shown is an intraocular lens 1 free of any external compressive forces, i.e. outside of the confines of the capsular bag 14. A line X-X is shown dividing the circular perimeter of the optic 2 into a first semicircular region 4 and a second semicircular region 5. Both haptics 6 of the first pair 12 may join with the optic periphery 3 at the first semicircular region 4 whereas both haptics of the second pair 13 may join with the optic periphery 3 at the second semicircular region 5. In an embodiment both haptics 6 of the first pair 12 may meet with the optic periphery 3 toward opposite ends of the first semicircular region 4, whereas both haptics 6 of the second pair 13 may meet with the optic periphery 3 toward opposite ends of the second semicircular region 5. The intraocular lens 1 may exhibit symmetry about line X-X.

Also shown in FIG. 2 is a line Y-Y that bisects with line X-X to divide the optic 2 with a circular perimeter into four equal quadrants. In an embodiment, each of the two haptics 6 of the first pair 12 may meet with the optic periphery 3 at different but adjacent quadrants. Similarly, each of the two haptics 6 of the second pair 13 may meet with the optic periphery 3 at different but adjacent quadrants which are both different to the two quadrants by which the haptics 6 of the first pair 12 join. The span of each of the arcuate haptics 6 may curve toward line Y-Y such that the distal end 9 of each haptic 6 is in nearer relation to Y-Y than the proximal end 8. Further, the concavity of each of the haptics 6 may be orientated toward line Y-Y. The intraocular lens 1 may exhibit symmetry about line Y-Y.

Lines X-X and Y-Y intersect at the centre point C of the circular perimeter of the optic 2. Shown in FIG. 2 is a line A drawn from centre point C through the junction of the inner edge 11 of the proximal end 8 of the haptic 6. Also shown in FIG. 2 is a line B drawn from centre point C to touch with an extreme of the distal end 9 of the same haptic 6 through which line A is drawn. Each haptic 6 may be configured to span a sizable portion of the quadrant to the optic periphery 3 to which it attaches, as measured by the included angle between lines A and B. In an embodiment, the included angle between lines A and B may be between about 30° to about 50°, or about 40°. In an embodiment, the included angle between A and B may be between about 35° to about 45° or about 40°. The included angle between line B and between line Y-Y may be between about 5° to about 20°, or between about 10° to about 15°. The included angle between line A and between line X-X may be between about 30° to about 50°, or between about 35° to about 45°, or about 40°. The offset between the inner edge 11 of the distal end 9 of the haptic 6 and the optic periphery 3 along line B may be between about 2 mm to 3 mm, or about 2.5 mm. The offset between the opposing distal ends 9 of the two haptics 6 of both the first pair 12 and the second pair 13 may be between about 2 mm to about 3 mm, or about 2.5 mm. The span of each haptic 6 measured between the extremes of the proximal end 8 of the haptic 6 and the distal end 9 of the haptic 6 along the arcuate curve of the haptic 6 may be between about 3 mm to about 6 mm, or about 4.5 mm. The radius of curvature (arc) of each curve-form haptic 6 may be between about 4 mm to about 6 mm, or about 5 mm.

The thickness of the haptic 6, as measured between the outer edge 10 and the inner edge 11 may vary from the proximal end 8 to the distal end 9. The thickness may taper from the proximal end 8 to the distal end 9. In an embodiment, the thickness of the haptic 6 at the proximal end 8 may be about 0.5 mm to about 0.7 mm, or about 0.6 mm, and the thickness of the distal end 9, immediately adjacent to the bulge 17, may be about 0.3 mm to about 0.5 mm, or about 0.4 mm. The thickness of the haptic 6 measured between the anterior and posterior faces, which is the thickness in a direction into the page of the depicted embodiments, may be about 0.4 mm to about 0.5 mm. In an embodiment, the haptic 6 may feature a recess 16 along its span, forming an area of minimum thickness. In the depicted embodiments, the recess 16 may be formed into the inner edge of the haptic 6. The recess 16 may have a radius of about 0.1 mm to about 0.3 mm, or about 0.2 mm. The recess 16 may be formed into the haptic 6 at about a fifth, or about a quarter of the span of the haptic 6 nearer to the proximal end 8. The provision of a recess 16 in this manner may promote bending of the haptic 6 at an optimal position when under compression from the capsular bag 14. The provision of a recess 16 in this manner may further reduce the outward pressure of the haptic 6 on the capsular bag 14.

In an embodiment, the haptics 6 may angle toward an anterior direction, which is toward the eye when the intraocular lens 1 is in a fitted condition, by about 0.5° to about 5°.

The presently described intraocular lens 1 having four haptics 6 meeting with the optic 2 at different points about the optic periphery 3 may improve the stability of the lens within the capsular bag 14. This improved stability may be present in all directions and planes, including rotational stability, horizontal and vertical stability, anterior and posterior stability and lens tilt stability. Such improved stability may make the presently described intraocular lens 1 particularly suitable for use with optics requiring high levels of stability, such as multifocal, bifocal and toric intraocular lenses.

EXPERIMENTAL SIMULATION

A Finite Element Analysis (FEA) was carried out following the simulation of the physical phenomenon acting on an embodiment of the intraocular lens as herein described when in situ using the numerical technique Finite Element Method (FEM). FIGS. 3, 4, 5 and 6 provide progressive images depicting the results of the FEM on the intraocular lens as compressive forces are applied to the four haptics.

The FEA demonstrates the intraocular lens deformed at various diameters between 12.4 mm and 9.0 mm. At all diameters, the deformed intraocular lens showed no stress on the optic which is important so that vision is not affected by the optic irregularities. The FEA demonstrates the flexibility of the intraocular lens and the varying relationship of the haptics to each other and to the optic.

Many modifications will be apparent to those skilled in the art without departing from the scope of the present invention.

The invention claimed is:

1. An intraocular lens comprising an optic and four haptics extending from the optic, each haptic having a proximal end meeting with the optic at differing points about a periphery of the optic, wherein the four haptics are arranged into:
   a first pair comprising two arcuate haptics with curvature orientated toward each other such that a distal end of each of the two haptics of the first pair are in nearer relation than their proximal ends; and,
   a second pair comprising two arcuate haptics with curvature orientated toward each other such that a distal end of each of the two haptics of the second pair are in nearer relation than their proximal end,
   wherein an outer edge of at least one of the four haptics has a rounded bulge configured to engagingly fit into a lacuna of a capsular bag of a patient when in use; and
   wherein the rounded bulge is configured with a curved perimeter with a radius of curvature of about 0.1 mm to 0.3 mm.

2. The intraocular lens according to claim 1, wherein the optic periphery is circular.

3. The intraocular lens according to claim 2, wherein both haptics of the first pair meet with the optic periphery at a first semicircular region of the optic and both haptics of the second pair meet with the optic periphery at a second semicircular region of the optic, wherein the first and second semicircular regions do not overlap.

4. The intraocular lens according to claim 2, wherein each haptic meets with the optic periphery at a separate quadrant of the optic.

5. The intraocular lens according to claim 4, wherein the first pair of haptics meet with the optic periphery at adjacent quadrants of the optic and the second pair of haptics meet with the optic periphery at adjacent quadrants of the optic.

6. The intraocular lens according to claim 1, wherein the haptics of the first pair have generally opposing concavities and the haptics of the second pair have generally opposing concavities.

7. The intraocular lens according to claim 1, wherein each of the four haptics has a thin, elongate form.

8. The intraocular lens according to claim 1, wherein each of the four haptics has a solid cross section across its entire span.

9. The intraocular lens according to claim 1, wherein the intraocular lens is of one-piece construction.

10. The intraocular lens according to claim 1, wherein the rounded bulge is at the distal end of the at least one of the four haptics.

11. The intraocular lens according to claim 1, wherein the intraocular lens is formed of a foldable material.

12. The intraocular lens according to claim 11, wherein the foldable material has memory.

13. The intraocular lens according to claim 11, wherein the intraocular lens formed of the foldable material is suitable for use with a preloaded injection system.

* * * * *